United States Patent [19]

Dolak et al.

[11] Patent Number: 4,600,758

[45] Date of Patent: Jul. 15, 1986

[54] ISOINDOLE DERIVATIVES

[75] Inventors: Terence M. Dolak; Tellis A. Martin, both of Evansville, Ind.

[73] Assignee: Mead Johnson & Company, Evansville, Ind.

[21] Appl. No.: 667,779

[22] Filed: Nov. 1, 1984

Related U.S. Application Data

[62] Division of Ser. No. 441,204, Nov. 12, 1982, Pat. No. 4,495,194.

[51] Int. Cl.$^4$ .......................................... C07D 401/04
[52] U.S. Cl. .................................................. 546/200
[58] Field of Search ........................................ 546/200

[56] References Cited

U.S. PATENT DOCUMENTS 3,579,524  5/1971  Van Dyke ........................ 546/200

FOREIGN PATENT DOCUMENTS 0026749  4/1981  European Pat. Off. ............ 546/200
1425578  2/1976  United Kingdom ............... 546/200
1486104  9/1977  United Kingdom ............... 546/200

OTHER PUBLICATIONS

Topliss, J., J. Med. Chem., 15 (10), 1006 (1972).
Cornish, E., et al., J. Pharm. Pharmac., 18, 65-80, (1966).
Chem. Abstracts, 81:58265d, (1974) [Suzuki, et al., Nippon Yakurigaku Zasshi, 1972, 68, (3), 276-89].
Chem. Abstracts, 90:97589t, (1979), [Himori, et al., Jpn. J. Pharmacol. 1978, 28, (6), 811-18].

Primary Examiner—Richard A. Schwartz
Attorney, Agent, or Firm—Robert H. Uloth; Richard P. Ryan

[57] ABSTRACT

Novel phthalimide intermediates are reduced to 5-sulfamoyl-6-halo-3-oxoisoindole compounds bearing a substituted 1-phenylalkyl-4-piperidinyl moiety as the isoindole N-substitutent. Preferred compounds such as 6-chloro-2,3-dihydro-3-oxo-2-[1-(phenylmethyl)-4-piperidinyl]-1H-isoindole-5-sulfonamide exhibit diuretic and antihypertensive properties.

3 Claims, No Drawings

ISOINDOLE DERIVATIVES

This is a divisional application of application Ser. No. 441,204 filed 11/12/82, now U.S. Pat. No. 4,495,194.

FIELD OF THE INVENTION

This invention relates to isoindole derivatives, pharmaceutically acceptable salts thereof and to processes for synthesis thereof. Other aspects of the invention concern pharmaceutical compositions containing an instant compound as active ingredient and methods of treatment where there is an indicated need for an antihypertensive and/or diurectic agent.

DESCRIPTION OF THE PRIOR ART

European Patent Application No. 26,749 discloses 2-benzylpiperidinyl-phthalimidine derivatives useful as antipsychotic agents of the following general formula (1)

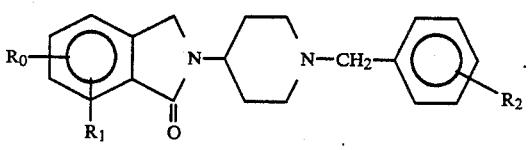

wherein $R_0$, $R_1$, and $R_2$ are independently hydrogen, halogen, $C_{1-3}$ alkyl, $C_{1-3}$ alkoxy, or trifluoromethyl. The compounds of (1) are reportedly neuropharmacologically active and useful for treating psychotic disorders, especially schizophrenia and mania.

Cornish, et al, J. Pharm. Pharmacol., 18, 65–80 (1966) discloses preparation of phthalimides and 1-oxoisoindolines related to the diuretic chlorexolone (2).

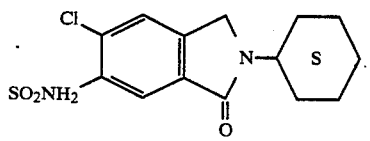

Himor, et al, Jpn. J. Pharmacol. 1978, 28(6), 811–818; (Chem. Abs. 90:97589t) studied the antihypertensive effect of a combination of clorexolone and the β-adrenergic blocking agent, alprenolol in conscious renal hypertensive dogs and found a significant decrease in blood pressure after the second day of treatment.

Suzuki, et al, Nippon Yakurigaku Zasshi, 1972, 68(3), 276–289 (Chem. Abs. 81:58265d) reported that the hypotensive diuretics, hydroflumethiazide, trimaterene, clorexolone, etc. have favorable effects in the spontaneously hypertensive rat.

SUMMARY AND DETAILED DESCRIPTION OF THE INVENTION

In its broadest aspect, the present invention is concerned with 3-oxoisoindole derivatives having antihypertensive and/or diuretic properties characterized by a compound of Formula I

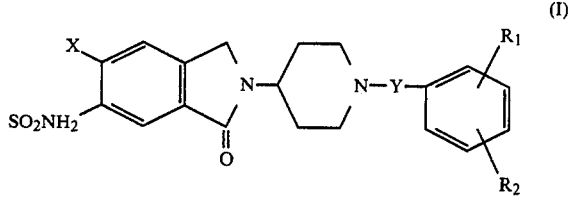

wherein X is halogen or trifluoromethyl; $R_1$ and $R_2$ are independently hydrogen, lower alkyl, lower alkoxy, lower alkenyloxy, lower alkylthio, trifluoromethyl, cyano, or nitro; Y is a single bond or a divalent straight or branched chain alkylene radical of 1 to 4 carbon atoms inclusive; or a pharmaceutically acceptable acid addition salt thereof.

Other contemplated classes of compounds within the ambit of Formula I are those defined as:

(1) X is halogen; $R_1$ and $R_2$ are independently hydrogen, lower alkyl, lower alkoxy, lower alkenyloxy, lower alkylthio, trifluoromethyl, cyano, nitro; and Y is —$CH_2$—.

(2) X is halogen, $R_1$ is hydrogen, lower alkyl, lower alkoxy, lower alkenyloxy, lower alkylthio, trifluoromethyl, cyano, nitro, $R_2$ is hydrogen; and Y is —$CH_2$—.

(3) X is halogen; $R_1$ is hydrogen, lower alkyl, lower alkoxy, lower alkoxy, lower alkenyloxy, trifluoromethyl; $R_2$ is hydrogen; and Y is —$CH_2$—.

(4) X is chlorine, $R_1$ is hydrogen, lower alkyl, lower alkoxy, lower alkenyloxy, trifluoromethyl; $R_2$ is hydrogen, and Y is —$CH_2$—.

(5) X is halogen; $R_1$ and $R_2$ are hydrogen; and Y is —$CH_2$—.

It is to be understood that by employment of the term "lower alkyl" and "lower alkoxy" herein, it is meant that the carbon chains of each group include both straight and branched carbon radicals containing up to 6 carbon atoms, preferably not more than 4 carbon atoms. Exemplary of carbon chain radicals are methyl, ethyl, isopropyl, 1-butyl, 1-methylpropyl, 2-methylpropyl, tert.-butyl, hexyl and the like. Further the term "halogen" used herein connotes all members of that group but preferably chlorine, bromine and fluorine.

The pharmaceutically acceptable acid addition salts of the invention are those in which the anion does not contribute significantly to toxicity or pharmacological activity of the salt, and therefore are considered pharmacological equivalents of Formula I bases.

For purposes of salt formation of the substances of Formula I, there may be mentioned pharmaceutical acceptable acids such as hydrochloric and other hydrohalic acids, sulphuric, phosphoric, nitric, aliphatic, alicyclic, aromatic or heterocyclic carboxylic acids or sulphonic acids, such as formic, acetic, propionic, succinic, glycollic, lactic, malic, tartaric, citric, ascorbic, maleic, hydroxymaleic or pyruvic, fumaric, benzoic, p-amino-benzoic, anthranilic, p-hydroxybenzoic, salicyclic, or p-aminosalicyclic, methanesulphonic, ethanesulphonic, hydroxyethanesulphonic, ethylenesulphonic; halogenobenzenesulphonic acid, toluenesulphonic acid, naphthalenesulphonic acid or sulphanilic acid.

Conventional methods are used to prepare the salts. Thus, admixture of a Formula I base with the selected acid in an inert solvent such as water, ethyl acetate, methanol, dimethylformamide and the like with salt isolation by conventional concentration or crystallization techniques are employed.

The Formula I salts are, in some instances, obtained in hydrated form, e.g., hemihydrates, monohydrates, sesquihydrates; and it is to be understood that such forms are within the ambit of the instant invention.

According to the present invention, the compounds characterized by Formula I

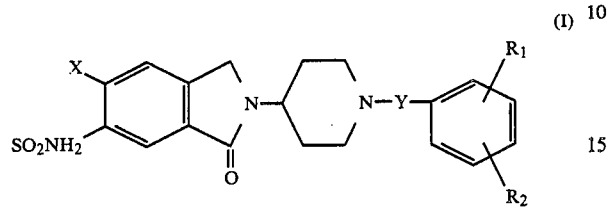

(I)

wherein X is halogen or trifluoromethyl; $R_1$ and $R_2$ are independently hydrogen, lower alkyl, lower alkoxy, lower alkenyloxy, lower alkylthio, trifluoromethyl, cyano, or nitro, and Y represents a single bond or a divalent straight or branched chain alkylene radical of 1 to 4 carbon atoms are obtained by a method comprising
(a) reducing a 1,3-dioxoisoindole compound of Formula II or a 1-hydroxy-3-oxoisoindole compound of Formula III

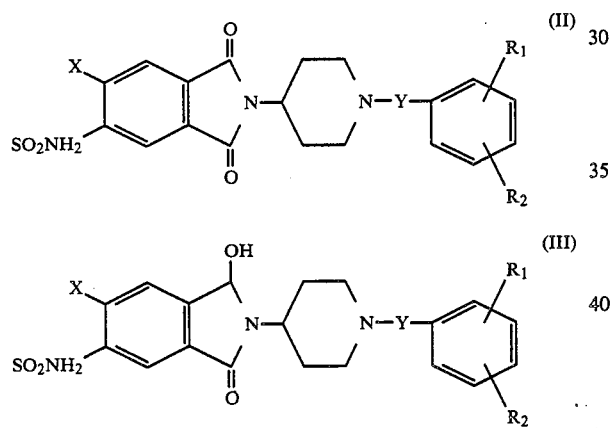

(II)

(III)

wherein X, $R_1$, $R_2$ and Y are as defined above; or
(b) reacting a 4-aminopiperidine compound of Formula IV

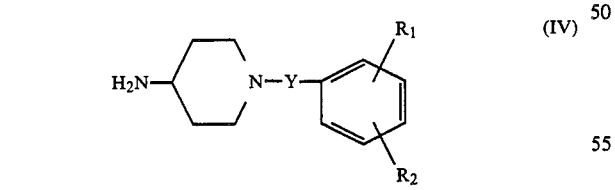

(IV)

wherein $R_1$, $R_2$ and Y are as defined above with a sulfamoyl compound of Formula V in an inert solvent

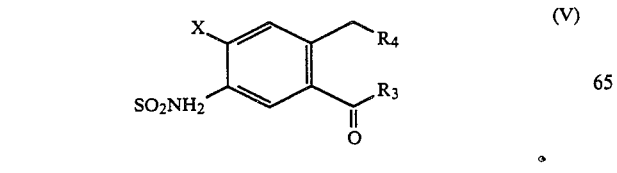

(V)

wherein X is as defined above, $R_3$ is amino, halogen, lower alkoxy; and $R_4$ is halogen or taken as the radical $R_4CH_2$— is carbamoyl or formyl; and $R_3$ and $R_4$ taken together is oxygen;
(c) reacting a piperidinyl compound of Formula VI

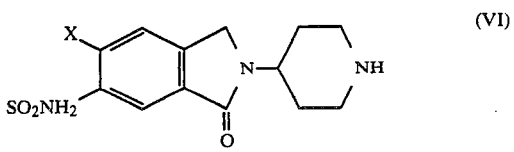

(VI)

with a phenylalkyl compound of Formula VII

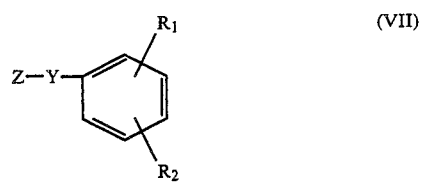

(VII)

wherein X, $R_1$, $R_2$, and Y are as defined above and Z is a reactive leaving group.

Reduction of the 1,3-dioxoisoindole compounds of Formula II or 1-hydroxy-3-oxoisoindoles of Formula III is carried out with zinc and acetic acid or tin and concentrated hydrochloric acid at elevated temperatures generally ranging from 60°–150° for periods of about 6–48 hours in a reaction inert organic solvent. In the case of zinc-acetic acid, temperatures of 100°–150° are preferred and the reduction is conveniently carried out in acetic acid at reflux temperature. Further, reduction with zinc-acetic acid is particularly preferred in that the compounds of Formula I are readily purified by conventional techniques such as basification, extraction and trituration of the extract or precipitation of acid addition salts from crude extracts. In the case of the tin/concentrated hydrochloric acid reduction, preferably carried out at 60°–100° in methanol, the Formula I products are more difficult to purify, in some instances, in that they form relatively stable complexes with tin salts. Treatment of the tin complexed Formula I products with hydrogen sulfide under acedic conditions or tetramethylethylenediamine in an inert solvent such as methanol removes the tin as the insoluble sulfide or tetramethylethylenediamine complex, respectively, to provide pure products with respect to elemental analysis but with traces of tin as demonstrated by flame spectrophotometry. Reduction of Formula II and Formula III compounds may be carried out by other conventional means such as use of light metal hydrides.

The compounds of Formula III considered part of the present invention have antihypertensive and/or diuretic activity and are obtained by reduction of the corresponding 1,3-dioxoisoindole with excess zinc in acetic acid below 100°, preferably at or near room temperature.

The intermediates of Formula IV can be prepared by artrecognized methods involving stepwise use of an amino protecting group such as tert.-butoxycarbonyl, catalytic debenzylation, N-alkylation with a phenylalkyl halide and finally removal of the protecting group as illustrated by the following reaction scheme.

PREPARATION OF FORMULA IV INTERMEDIATES

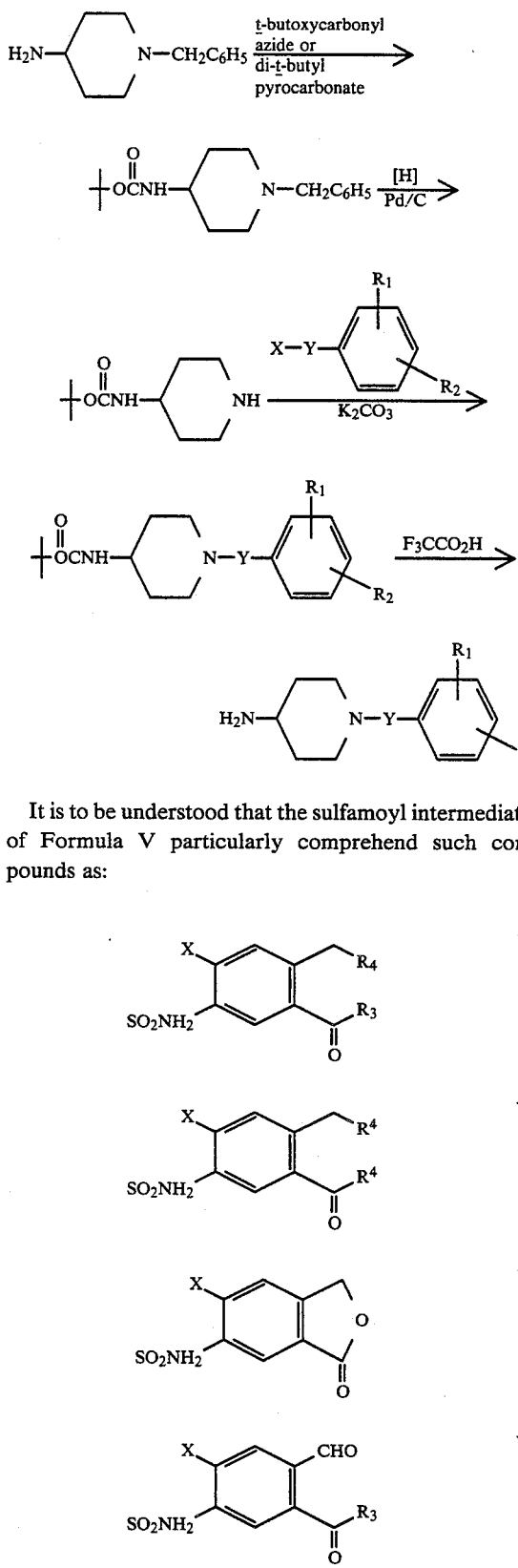

It is to be understood that the sulfamoyl intermediates of Formula V particularly comprehend such compounds as:

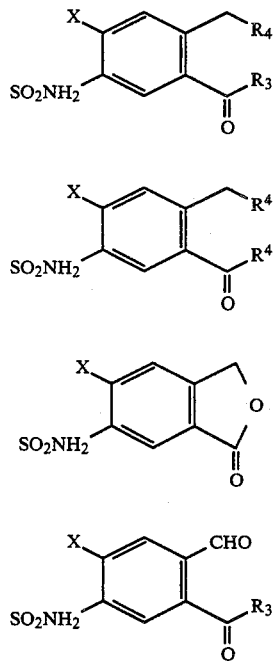

wherein X is halogen or trifluoromethyl, R$_3$ is lower alkoxy, preferably methoxy and R$_4$ is halogen.

Knowm methods are employed in preparation of the Formula V and VI intermediates as illustrated by European Patent Application No. 26,749, supra.

Regarding the reaction of a piperidinyl compound of Formula VI with a phenylalkyl compound of Formula VII, an inert organic solvent such as n-pentanol or dimethylformamide is employed at elevated temperature of from about 50°–200° in the presence of a basic condensation agent, preferably an alkali metal hydroxide, carbonate or bicarbonate, for example sodium carbonate, potassium carbonate, sodium bicarbonate or potassium bicarbonate, or an organic tertiary nitrogen amine bases; such as triethylamine or pyridine. The Formula VI intermediate is obtained from a compound of Formula I wherein the N-phenylalkyl radical is benzyl by catalytic debenzylation. Phenylalkyl compounds of Formula VII are commercially available or conventionally prepared. The term "reactive leaving group" as used with respect to "Z" in Formula VII refers to a reactive esterified hydroxy group such as that obtained when esterified by strong inorganic or organic acids such as hydrochloric, hydrobromic, hydroiodic acid, sulfuric acid, or an organic sulfonic acid, for example, benzenesulfonic, p-bromobenzenesulfonic or p-toluenesulfonic acid. Particularly preferred leaving groups are chlorine or bromine.

The compounds of Formula I have antihypertensive and/or diuretic properties as can be demonstrated by standard pharmacological test models known to correlate with effects in man. With respect to antihypertensive utility, there can be mentioned such conventional models as the spontaneously hypertensive and DOCA-salt hypertensive rat. Typical tests are conducted as follows:

Spontaneously Hypertensive Rat

Male rats weighing 300–400 g, previously conditioned to the procedure, are prewarmed in a heating chamber (30° C.) for 10–20 min. and subsequently restrained in a wire holder at that temperature. Systolic blood pressure and heart rate are measured by the tail-cuff technique using a pneumatic pulse transducer and a biotachometer before, and 2, 4, and 24 hours after oral administration of vehicle (0.25% Methocel in water) or test compounds suspended in vehicle at a dose volume equivalent to 5 ml/kg. Blood pressure and heart rate data are reported as changes from zero-hour measurements with vehicle control groups run periodically to confirm that the vehicle has no effect.

DOCA-salt Hypertensive Rat

Male rates initially weighing 80–100 g, are made hypertensive by injecting 10 mg. of deoxycorticosterone acetate (DOCA) subcutaneously three times a week for three weeks providing 1% saline ad libitum. After the tenth DOCA injection, the 1% saline is replaced with distilled water. One week later, animals are anesthetized with methoxyflurane and a catheter advanced into the aorta via the left common carotid artery to record mean arterial blood pressure (MAPB) and heart rate. The heparin-filled catheter is passed beneath the skin and exteriorized behind the head. Two days later, MABP and heart rate are determined before and four hours after oral administration of vehicle (0.25% Methocel in 0.9% saline) or test compound suspended in vehicle at a dose volume equivalent to 5 ml/kg.

With respect to diuretic utility there can be mentioned the conscious rat diuretic screen of Lipschitz, et al (J. Pharmcol. Exp. Therap. 79–97 (1943)). In this test, dose response assays of diuretic, natruiretic and kaliuretic activity are determined by oral administration of the test substance.

Preferred compounds of the invention are those which have both diuretic and antihypertensive action. This dual activity is particularly advantageous in the treatment of hypertension since the diuretic effect (reduced plasma volume) associated with antihypertensive activity is complimented by the antihypertensive action which produces an effect by a mechanism other than diuresis. A representative and particularly preferred compound, "6-chloro-2,3-dihydro-3-oxo-2-[1-(phenylmethyl)-4-piperidinyl]-1H-isoindole-5-sulfonamide" (referred to herein as MJ 14712) has a dose-dependent diuretic/natriuretic response in a dose range of 0.3 to 3.0 mg/kg body weight. As an antihypertensive, MJ 14712 shows activity in the DOCA-hypertensive rat and spontaneously-hypertensive rat. In the latter, MJ 14712 exhibits a dose-dependent decrease in systolic blood pressure following doses of 3 to 100 mg/kg body weight some onset of the antihypertensive effect seen at about two hours.

Aside from diuretic and antihypertensive properties, MJ 14712 has calcium channel blocking and vasodilating activity.

As stated above, Formula I compounds have diuretic and/or antihypertensive properties with those having complimentary diuretic and antihypertensive activity preferred. Thus, another embodiment of the instant invention is directed to a process for treating hypertension comprising systemically administering to a mammal in need of such treatment an antihypertensive effective amount of a compound of Formula I or a pharmaceutically acceptable acid addition salt thereof. By systemic administration, it is intended to include both oral and parenteral routes with oral being preferred. Examples of parenteral administration are intramuscular, intravenous, intraperitoneal, rectal and subcutaneous administration. The dosage will vary with the form of administration and the particular compound chosen. However, from about 0.05 to 500 per kg. of body weight of a mammal of a compound characterized by Formula I administered in effective single or multiple dosage units is generally satisfactory. In accordance with conventional clinical practice, an antihypertensive agent of Formula I is administered at a dosage substantially less than the dose of the compound which is thought to be effective. If the antihypertensive response is insufficient after a suitable trial, dosage is increased by small increments until the optimum antihypertensive effect is reached.

In carrying out the antihypertensive process, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

6-Chloro-2,3-dihydro-3-oxo-2-[1-(phenylmethyl)-4-piperidinyl]-1H-isoindole-5-sulfonamide

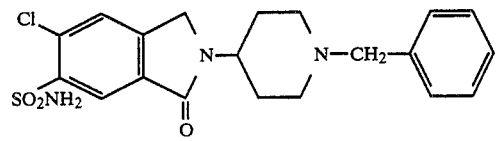

(a)
6-Chloro-2,3-dihydro-1,3-dioxo-2-[1-(phenylmethyl)-4-piperidinyl]-1H-isoindole-5-sulfonamide A mixture of 4-chloro-5-sulfamoylphthalimide (5.6 g., 0.02 mole) and 4-amino-1-benzylpiperidine (3.8 g, 0.02 mole) in 50 ml. of n-pentanol was heated at 136°–138° for 16 hr., cooled and filtered. During reflux, a gas inlet tube was placed below the solvent surface and dry nitrogen bubbled through the solution to facilitate removal of generated ammonia. The filter-cake washed with 100 ml. of 1:5 dioxane-n-hexane and dried in vacuo yielded 5.8 g. (67%) of product (a), m.p. 256°–258° (dec.). A sample crystallized from dimethylformamide-ethanol provided analytically pure 6-chloro-2,3dihydro-1,3-dioxo-2-[1-(phenylmethyl)-4-piperidinyl]-1H-isoindole-5-sulfonamide, m.p. 258°–259° (dec.).

Anal. Calcd. for $C_{20}H_{20}ClN_3O_4S$: C, 55.37; H, 4.65; N, 9.68. Found: C, 55.52; H, 4.68; N, 10.01.

NMR (DMSO-$d_6$): 1.68 (2H, m); 2.15 (4H, m); 2.93 (2H, m); 3.50 (2H, s); 4.00 (1H, m); 7.33 (5H, s); 8.00 (2H, bs); 8.13 (1H, s); 8.30 (1H, s).

A scaled-up 0.3 mole preparation refluxed for a 10 hr. period provided 108.4 g. (83%) of product, m.p. 258°–259° (dec.).

(b) Tin-hydrochloric Acid Reduction of 6-Chloro-2,3-dihydro-1,3-dioxo-2-[1-(phenylmethyl)-4-piperidinyl]-1H-isoindole-5-sulfonamide A mixture of the above part (a) 1,3-dioxoisoindole (4.4 g., 0.01 mole), and 30 mesh granulated tin (2.8 g., 0.024 mole) in 20 ml. of methanol and 12 ml. of concentrated hydrochloric acid was heated at 75°–80° for a 8 hr. period. Additional 1 g. portions of tin were added at the end of 5 hr. and 6 hr., respectively. After cooling, the reaction mixture was diluted with 40 ml. of methanol, heated to reflux and filtered through infusorial earth to remove unreacted tin. The filter-cake was washed with methanol and combined filtrates concentrated under reduced pressure. Residual oil slurried with warm methanol provided 1 g. of solid and cooling of the methanol decant an additional 2.1 g. of solid. The combined crude product was further purified by stirring with 65 ml. of 0.077N hydrochloric acid while slowly introducing a gaseous stream of hydrogen sulfide ($H_2S$) during a 2.0 hr. period. Excess $H_2S$ was removed under reduced pressure, the mixture filtered through infursorial earth and the filter-cake extracted with warm methanol. Cooling the methanol filtrates provided 2.2 g. of product which crystallized from methanol-water gave analytically pure 6-chloro-2,3-dihydro-3-oxo-2-[1-(phenylmethyl)-4-piperidinyl]-1H-isoindole-5-sulfonamide hydrochloride as the monohydrate, m.p. 282°–284°.

Anal. Calcd. for $C_{20}H_{22}ClN_3O_3S.HCl.H_2O$: C, 50.63; H, 5.31; N, 8.86; $H_2O$, 3.80. Found: C, 50.55; H, 5.13; N, 8.88; $H_2O$, 4.20.

NMR (DMSO-$d_6$): 1.91 (2H, m); 2.29 (2H, m); 3.23 (4H, m); 3.34 (2H, bs); 4.28 (2H, s); 4.36 (1H, m); 4.50 (2H, s); 7.47 (3H, m); 7.60 (2H, m); 7.76 (2H, bs); 7.96 (1H, s); 8.20 (1H, s).

Reduction of the part (a) 1,3-dioxoisoindole with metallic tin and hydrochloric acid with removal of residual ionic tin by treatment with $H_2S$ under acidic conditions was repeated to give hydrated 6-chloro-2,3-dihydro-3-oxo-2-[1-(phenylmethyl)-4-piperidinyl]-1H-isoindole-5-sulfonamide hydrochloride in yields ranging from 30–45%. The degree of hydration appears to be generally dependent upon drying conditions and is usually within the range of ¼ to 1.5 mole equivalent of water. Melting points of hydrated products were affected by rate of heating.

(c) Zinc-acetic Acid Reduction of 6-Chloro-2,3-dihydro-1,3-dioxo-2-[1-(phenylmethyl)-4-piperidinyl]-1H-isoindole-5-sulfonamide Zinc dust (12.4 g., 0.189 mole) was added in one portion to 1,3-dioxoisoindole (15.0 g., 0.034 mole) of part (a) in 300 ml. of acetic acid. The reaction mixture was stirred at room temperature for 0.5 hr. and then heated to reflux for a 6 hr. period during which time additional 3.0 g. portions of zinc were added at the end of 3, 4, and 5 hr., respectively. After stirring overnight, the reaction mixture was filtered and the filtrate concentrated to dryness under reduced pressure with additional water added to the residue and removed in vacuo to remove traces of acetic acid. Residual material was slurried in water, filtered and the filtrate concentrated to dryness. The product was stirred with hot ethyl acetate and saturated sodium bicarbonate solution and the separated ethyl acetate fraction dried over $MgSO_4$ and concentrated to a small volume. After cooling, precipitated material was collected to provide the free base 6.03 g., m.p. 232°–235° (dec.). The free base taken up in dimethylformamide, acidified with ethaolic hydrogen chloride and diluted with absolute ethanol afforded 7.6 g., (49% yield) of product which was crystallized from 1:1 methanol-water to provide analytically pure hydrated 6-chloro-2,3-dihydro-3-oxo-2-[1-phenylmethyl)-4-piperidinyl]-1H-isoindole-5-sulfonamide hydrochloride, m.p. 271°–272° (dec.).

Anal. Calcd. for $C_{20}H_{22}ClN_3O_3S.HCl.2/3H_2O$: C, 51.29; H, 5.23; N, 8.97; $H_2O$, 2.56. Found: H, 51.34; H, 5.04; N, 9.04; $H_2O$, 3.16.

NMR (DMSO-$d_6$): 1.91 (2H, m); 2.29 (2H, m); 3.23 (4H, m); 3.31 (1.5H, bs); 4.30 (2H, s); 4.36 (1H, m); 4.50 (2H, s); 7.46 (3H, m); 7.65 (2H, m) 7.76 (2H, bs); 7.94 (1H, s); 8.19 (1H, s); 11.40 (1H, bs).

(d) 6-Chloro-2,3-dihydro-3-oxo-2-[1-(phenylmethyl)-4-piperidinyl]-1H-isoindole-5-sulfonamide A mixture of 4.7 g. of hydrated 6-chloro-2,3-dihydro-3-oxo-2-[1-(phenylmethyl)-4-piperidinyl]-1H-isoindole hydrochloride prepared by tin-hydrochloric acid reduction and 0.84 g of sodium bicarbonate in 140 ml. of 50% methanol was maintained at 45°–55° for a 4 hr. period, filtered and the filter-cake washed with water and methanol to afford 3.8 g. of white solid. Crystallization of this material from dimethylformamide-methanol afforded analytically pure free base "6-chloro-2,3-dihydro-3-oxo-2-[1-(phenylmethyl)-4-piperidinyl]-1H-isoindole-5-sulfonamide", m.p. 248°–250° (dec.) as the hemihydrate.

Anal. Calcd. for $C_{20}H_{22}ClN_3O_3S.0.5H_2O$: C, 56.00; H, 5.40; N, 9.80, $H_2O$, 2.10. Found: C, 56.37; H, 5.23; N, 9.90; $H_2O$, 2.34.

NMR (DMSO-$d_6$): 1.79 (4H, m); 2.00 (2H, m); 2.89 (2H, m); 3.48 (3H, m); 4.00 (1H, m); 4.51 (2H, s); 7.29 (5H, s); 7.77 (2H, bs); 7.84 (1H, s); 8.22 (1H, s).

(e) A sample of free base prepared by zinc-acetic acid reduction dried under reduced pressure/heat provided anhydrous 6-chloro-2,3-dihydro-3-oxo-2-[1-(phenylmethyl)-4-piperidinyl]-1H-isoindole-5-sulfonamide, m.p. 227°–229° (dec.).

Anal. Calcd. for $C_{20}H_{22}ClN_3O_3S$: C, 57.20; H, 5.28; N, 10.01. Found: C, 56.86; H, 5.26; N, 9.92.

NMR (DMSO-$d_6$): 1.75 (2H, m); 1.98 (4H, m); 2.90 (2H, m); 3.49 (2H, s); 4.00 (1H, m); 4.52 (2H, s); 7.29 (5H, s); 7.73 (2H, bs); 7.86 (1H, s); 8.20 (1H, s).

Melting point variations may be related to the reduction method with tin-hydrochloric acid generally providing somewhat higher melting points, possibly related to traces of tin generally ranging from 100–200 parts per million.

EXAMPLE 2

6-Chloro-2-[1-[(4-chlorophenyl)methyl]-4-piperidinyl]-2,3-dihydro-3-oxo-1H-isoindole-5-sulfonamide Hydrochloride

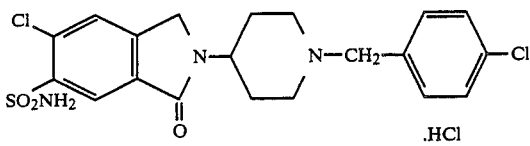

(a)
6-Chloro-2-[1-[(4-chlorophenyl)methyl]-4-piperidinyl]-2,3-dihydro-1,3-dioxo-1H-isoindole-5-sulfonamide Reaction of 4-chloro-5-sulfamoylphthalimide (5.57 g., 0.0214 mole) and 4-amino-1-(4-chlorobenzyl)piperidine (4.8 g., 0.0214 mole) in 85 ml. of n-pentanol according to the procedure of Example 1(a) with heating at 130°–138° for a 48 hr. period afforded 7.07 g. (71%) m.p. 248°–250° (dec.) of the 1,3-dioxoisoindole product. A sample crystallized from dimethylformamide-methanol provided analytically pure 6-chloro-2-[1-[(4-chlorophenyl)methyl]-4-piperidinyl]-2,3-dihydro-1,3-dioxo-1H-isoindole-5-sulfonamide, m.p. 250°–251° (dec.).

Anal. Calcd. for $C_{20}H_{19}Cl_2N_3O_4S$: C, 51.29; H, 4.09; N, 8.97. Found: C, 51.53; H, 4.21; N, 8.87.

(b) Title Product

Reduction of the above product (a) 1,3-dioxoisoindole (5.0 g., 0.0107 mole) with zinc and acetic acid according to the method of Example 1(c) and conversion of the free base (partially purified by trituration with ethyl acetate) to the hydrochloride salt in methanol afforded 6-chloro-2-[1-[(4-chloro-phenyl)-phenyl)-methyl]-4-piperidinyl]-2,3-dihydro-3-oxo-1H-isoindole-5-sulfonamide hydrochloride as the sesquihydrate, m.p. 256°–260° (dec.).

Anal. Calcd. for $C_{20}H_{21}Cl_2N_3O_3S \cdot HCl \cdot 1.5H_2O$: C, 46.39; H, 4.87; N, 8.11; $H_2O$, 5.22. Found: C, 46.76; H, 4.68; N, 8.26; $H_2O$, 5.74.

NMR (DMSO-$d_6$): 1.90 (2H, m); 2.30 (2H, m); 3.28 (4H, m); 3.33 (2H, bs); 4.30 (2H, s); 4.38 (1H, m); 4.50 (2H, s); 7.50 (2H, m); 7.71 (2H, m); 7.76 (2H, bs); 7.94 (1H, s); 8.19 (1H, s).

EXAMPLE 3

2-[1-[(4-Bromophenyl)methyl]-4-piperidinyl]-6-chloro-2,3-dihydro-3-oxo-1H-isoindole-5-sulfonamide Hydrochloride

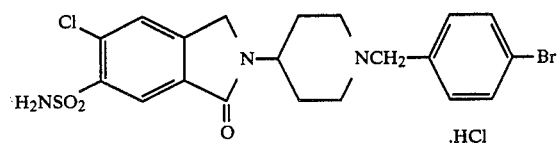

(a)
2-[1-[(4-Bromophenyl)methyl]-4-piperidinyl]-6-chloro-2,3-dihydro-1,3-dioxo-1H-isoindole-5-sulfonamide Reaction of a mixture of 4-chloro-5-sulfamoylphthalimide (6.48 g., 0.025 mole) and 4-amino-1-(4-bromobenzyl)piperidine (6.7 g., 0.025 mole) in n-pentanol according to the procedure of Example 1(a) afforded the 1,3-dioxoisoindole product. Purification of the crude product by triturating with n-heptane and crystallization from DMF-methanol afforded 6.9 g. (54%) of 2-[1-[(4-bromophenyl)methyl]-4-piperidinyl]-6-chloro-2,3-dihydro-1,3-dioxo-1H-isoindole-5-sulfonamide, m.p. 246°–247° (dec.).

Anal. Calcd. for $C_{20}H_{19}BrClN_3O_4S$: C, 46.84; H, 3.74; N, 8.19. Found: C, 46.99; H, 3.74; N, 8.31.

(b) Title Product

Reduction of the above part (a) 1,3-dioxoisoindole (6.15 g., 0.012 mole) with zinc in acetic acid according to method of Example 1(c) and conversion of the free base to the hydrochloride salt in methanol and crystallization from DMF-isopropanol afforded 2.08 g., (32%) of analytically pure hydrated 2-[1-[(4-bromophenyl)methyl]-4-piperidinyl]-6-chloro-2,3-dihydro-3-oxo-1H-isoindole-5-sulfonamide hydrochloride, m.p. 215°–227°.

Anal. Calcd. for $C_{20}H_{21}BrClN_3O_3S \cdot HCl \cdot 0.5H_2O$: C, 44.13; H, 4.26; N, 7.72; $H_2O$, 1.65. Found: C, 44.23; H, 4.58; N, 7.86; $H_2O$, 2.29.

NMR (DMSO-$d_6$): 1.90 (2H, m); 2.30 (2H, m); 2.24 (4H, m); 3.36 (2H, bs); 4.29 (2H, s); 4.35 (1H, m); 4.50 (2H, s); 7.64 (4H, s); 7.75 (2H, bs); 7.94 (1H, s); 8.20 (1H, s); 11.45 (1H, bs).

EXAMPLE 4

6-Chloro-2-[1-[(4-fluorophenyl)methyl]-4-piperidinyl]-2,3-dihydro-3-oxo-1H-isoindole-5-sulfonamide Hydrochloride

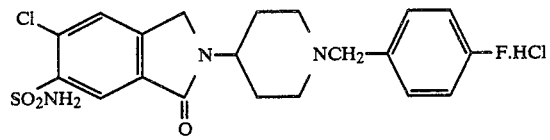

(a)
6-Chloro-2-[1-[(4-fluorophenyl)methyl]-4-piperidinyl]-2,3-dihydro-1,3-dioxo-1H-isoindole-5-sulfonamide Reaction of 4-chloro-5-sulfamoylphthalimide (8.86 g., 0.034 mole) and 4-amino-1-[(4-fluorophenyl)methyl]-piperidine (7.1 g., 0.034 mole) in 300 ml. of n-pentanol according to the procedure of Example 1(a) afforded 10 g. (65%) of the 1,3-dioxoisoindole product, m.p. 240°–242° (dec.). A sample crystallized from dimethyl-formamide-methanol-water provided analytically pure 6-chloro-2-[1-[(4-fluorophenyl)methyl]-4-piperidinyl]-2,3-dihydro-1,3-dioxo-1H-isoindole-5-sulfonamide, m.p. 245°–246° (dec.).

Anal. Calcd. for $C_{20}H_{19}ClFN_3O_4S$: C, 53.20; H, 4.24; N, 9.30. Found: C, 52.23; H, 4.22; N, 9.39.

(b) Title Product

Reduction of the above product (a) 1,3-dioxoisoindole (9.5 g., 0.021 mole) with zinc in acetic acid according to the procedure of Example 1(c), conversion of the free base of the hydrochloride salt and crystallization from methanol-water provided 1.5 g. (15%) of analytically pure hydrated 6-chloro-2-[1-[(4-fluorophenyl)methyl]-4-piperidinyl]-2,3-dihydro-3-oxo-1H-isoindole-5-sulfonamide hydrochloride, m.p. 285°–287° (dec.).

Anal. Calcd. for $C_{20}H_{21}ClFN_3O_3S \cdot HCl \cdot 0.8H_2O$: C, 49.15; H, 4.87; N, 8.60; $H_2O$, 2.95. Found: C, 49.38; H, 4.74; N, 8.50; $H_2O$, 3.36.

NMR (DMSO-d$_6$): 1.92 (2H, m); 2.30 (2H, m); 3.25 (4H, m); 3.32 (2H, bs); 4.30 (2H, s); 4.36 (1H, m); 4.50 (2H, s); 7.27 (2H, t, 9.0 Hz); 7.75 (4H, m); 7.95 (1H, s); 8.19 (1H, s); 11.45 (1H, bs).

EXAMPLE 5

6-Chloro-2-[1-[(2-chlorophenyl)methyl]-4-piperidinyl]-2,3-dihydro-3-oxo-1H-isoindole-5-sulfonamide Hydrochloride

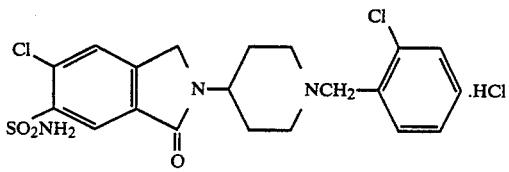

(a) 6-Chloro-2-[1-[(2-chlorophenyl)methyl]-4-piperidinyl]-2,3-dihydro-1,3-dioxo-1H-isoindole-5-sulfonamide Reaction of 4-chloro-5-sulfamoylphthalimide (8.3 g., 0.0316 mole) and 4-amino-1-(2-chlorophenyl)methyl piperidine (7.1 g., 0.0316 mole) in n-pentanol according to the procedure of Example 1(a) afforded 12.2 g. (82%) of the 1,3-dioxoisoindole product, m.p. 278°-279° (dec.). Crystallization of a sample from DMF-methanol provided analytically pure 6-chloro-2-[1-[(2-chlorophenyl)methyl]-4-piperidinyl]-2,3-1,3-dioxo-1H-isoindole-5-sulfonamide.

Anal. Calcd. for $C_{20}H_{19}Cl_2N_3O_4S$: C, 51.29; H, 4.09; N, 8.97. Found: C, 51.30; H, 4.28; N, 9.20.

(b) Title Product

Reduction of the above part (a) 1,3-dioxoisoindole (10 g., 0.021 mole) with zinc in acetic acid according to the method of Example 1(c), conversion of the free base to the hydrochloride salt and crystallization from methanol-water afforded 1.5 g., (14%) of analytically pure hydrated 6-chloro-2-[1-[(2-chlorophenyl)methyl]-4-piperidinyl]-2,3-dihydro-3-oxo-1H-isoindole-5-sulfonamide hydrochloride, m.p. 272°-274° (dec.).

Anal. Calcd. for $C_{20}H_{21}Cl_2N_3O_3S.HCl.1/2H_2O$: C, 48.06; H, 4.64; N, 8.41; H$_2$O, 1.80. Found: C, 48.00; H, 4.59; N, 8.39; H$_2$O, 2.25.

NMR (DMSO-d$_6$): 1.92 (2H, m); 2.35 (2H, m); 3.39 (5H, m); 4.50 (5H, m); 7.50 (3H, m); 7.75 (2H, bs); 7.94 (1H, s); 8.04 (1H, m); 8.19 (1H, s); 11.50 (1H, bs).

EXAMPLE 6

6-Chloro-2,3-dihydro-2-[1-[(4-methylphenyl)-methyl]-4-piperidinyl]-3-oxo-1H-isoindole-5-sulfonamide Hydrochloride

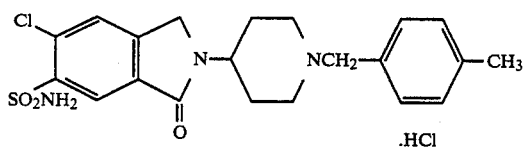

(a) 6-Chloro-2,3-dihydro-2-[1-[(4-methylphenyl)methyl]-4-piperidinyl]1,3-dioxo-1H-isoindole-5-sulfonamide Reaction of 4-chloro-5-sulfamoylphthalimide (7.8 g., 0.03 mole) and 4-amino-1-(4-methylbenzyl)piperidine (6.1 g., 0.03 mole) in 200 ml. of n-pentanol according to the procedure of Example 1(a) afforded 8 g. (60%) of product as a cream solid, m.p. 233°-235° (dec.). Crystallization of a sample from DMF-methanol provided analytically pure 6-chloro-2,3-dihydro-2-[1-[(4-methylphenyl)methyl]-4-piperidinyl]-1,3-dioxo-1H-isoindole-5-sulfonamide, m.p. 238°-240° (dec.).

Anal. Calcd. for $C_{21}H_{22}ClN_3O_4S$: C, 56.31; H, 4.95; N, 9.38. Found: C, 56.15; H, 5.03; N, 9.15.

(b) Title Product

Reduction of the above part (a) 1,3-dioxoisoindole (6.8 g., 0.0152 mole) with granulated tin and purification with H$_2$S/dilute hydrochloric acid according to the procedure of Example 1(b) with crystallization of the product from 50% methanol containing a trace of HCl afforded 1.3 g. (18%) of 6-chloro-2,3-dihydro-2-[1-[(4-methylphenyl)methyl]-4-piperidinyl]-3-oxo-1H-isoindole-5-sulfonamide hydrochloride as the monohydrate, m.p. 265°-267°.

Anal. Calcd. for $C_{21}H_{24}ClN_3O_3S.HCl.H_2O$: C, 51.64; H, 5.57; N, 8.60; H$_2$O, 3.69. Found: C, 51.94; H, 5.36; N, 8.62; H$_2$O, 3.76.

NMR (DMSO-d$_6$): 1.92 (2H, m); 2.32 (5H, m); 3.26 (4H, m); 3.33 (2H, bs); 4.23 (2H, s); 4.35 (1H, m); 4.50 (2H, s); 7.23 (2H, m); 7.55 (2H, m); 7.75 (2H, bs); 7.94 (1H, s); 8.20 (1H, s); 11.35 (1H, bs).

EXAMPLE 7

6-Chloro-2,3-dihydro-2-[1-[(2-methylphenyl)-methyl]-4-piperidinyl]-3-oxo-1H-isoindole-5-sulfonamide Hydrochloride

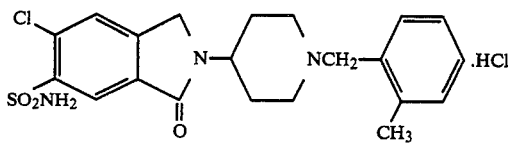

(a) 6-Chloro-2,3-dihydro-2-[1-[(2-methylphenyl)methyl]-4-piperidinyl]-1,3-dioxo-1H-isoindole-5-sulfonamide A mixture of 4-chloro-5-sulfamoylphthalimide (5.74 g., 0.022 mole) and 4-amino-1-[(2-methylphenyl)methyl]piperidine (4.5 g., 0.022 mole) in 85 ml. of n-pentanol was reacted according to the procedure of Example 1(a). Addition of n-heptane to the reaction mixture afforded 7.9 g. (80%) of the 1,3-dioxoisoindole product, m.p. 283°-243°. Crystallization of this material from DMF-methanol provided analytically pure 6-chloro-2,3-dihydro-2-[1-[(2-methylphenyl)methyl]-4-piperidinyl]-1,3-dioxo-1H-isoindole-5-sulfonamide, m.p. 244°-245° (dec.).

Anal. Calcd. for $C_{21}H_{22}ClN_3O_4S$: C, 56.31; H, 4.95; N, 9.38. Found: C, 56.49; H, 5.08; N, 9.39.

(b) Title Product

Reduction of the above part (a) 1,3-dioxoisoindole (5.0 g., 0.011 mole) with zinc in acetic acid according to the method of Example 1(c), conversion of the free base to the hydrochloride salt in methanol and crystallization from DMF-isopropanol afforded 1.8 g., (34%) of analytically pure 6-chloro-2,3-dihydro-2-[1-[(2-methylphenyl)methyl]-4-piperidinyl]-3-oxo-1H-isoindole-5-sulfonamide hydrochloride as the monohydrate, m.p. 280°-284°.

Anal. Calcd. for $C_{21}H_{24}ClN_3O_3S \cdot HCl \cdot H_2O$: C, 51.64; H, 5.57; N, 8.60; $H_2O$, 3.69. Found: C, 51.45; H, 5.59; N, 8.68; $H_2O$, 2.27.

NMR (DMSO-$d_6$): 1.90 (2H, m); 2.48 (5H, m); 3.39 (5H, m); 4.30 (2H, s); 4.35 (1H, m); 4.50 (2H, s); 7.29 (3H, m); 7.80 (3H, m); 7.92 (1H, s); 8.20 (1H, s); 11.15 (1H, bs).

EXAMPLE 8

6-Chloro-2,3-dihydro-2-[1-8 (4-methoxyphenyl)methyl]-4-piperidinyl]-3-oxo-1H-isoindole-5-sulfonamide

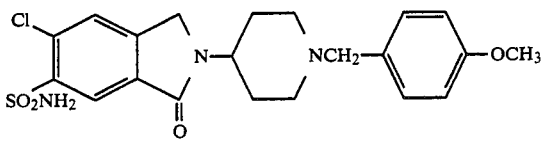

(a)
6-Chloro-2,3-dihydro-2-[1-[(4-methoxyphenyl)methyl]-4-piperidinyl]-1,3-dioxo-1H-isoindole-5-sulfonamide Reaction of 4-chloro-5-sulfamoylphthalimide (5.21 g., 0.02 mole) and 4-amino-1-(4-methoxybenzyl)piperidine (4.5 g., 0.02 mole) in 80 ml. of n-pentanol according to the procedure of Example 1(a) afforded the crude 1,3-dioxoisoindole product purified by chromatography (silica gel, ethyl acetate-n-hexane) to yield 2.88 g. (31%) of 6-chloro-2,3-dihydro-2-[1-[(4-methoxyphenyl)methyl]-4-piperidinyl]-1,3-dioxo-1H-isoindole-5-sulfonamide. The NMR spectral data was consistent for the compound used without further purification below.

(b) Title Product

Reduction of the above part (a) 1,3-dioxoisoindole (2.88 g., 0.0062 mole) with zinc and acetic acid according to the method of Example 1(c) and purification of the product as the free base from ethyl acetate afforded 1.37 g. (48%) of hydrated 6-chloro-2,3-dihydro-2-[1-[(4-methoxyphenyl)methyl]-4-piperidinyl]-3-oxo-1H-isoindole-5-sulfonamide, m.p. 207°–210°.

Anal. Calcd. for $C_{21}H_{24}ClN_3O_4S \cdot 0.8H_2O$: C, 54.31; H, 5.56; N, 9.04; $H_2O$, 3.10. Found: C, 54.19; H, 5.26; N, 8.77; $H_2O$, 2.34.

NMR (DMSO-$d_6$): 1.82 (4H, m); 2.10 (2H, m); 2.95 (2H, m); 3.48 (2H, s); 3.79 (3H, s); 4.05 (1H, m); 4.60 (2H, s); 6.94 (2H, m); 7.28 (2H, m); 7.82 (2H, bs); 7.94 (1H, s); 8.26 (1H, s).

EXAMPLE 9

6-Chloro-2,3-dihydro-2-[1-[2-(4-methoxyphenyl)-ethyl]-4-piperidinyl]-3-oxo-1H-isoindole-5-sulfonamide

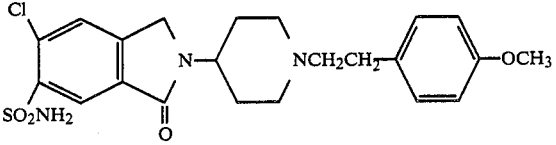

(a) 4-Chloro-5-(sulfamoyl)-1,2-benzenedicaboxamide

A solution of 4-chloro-5-sulfamoylphthalimide (21.3 g., 0.076 mole) and 250 ml. of liquid ammonia was stirred at room temperature while permitting ammonia to evaporate. Water was added to residual material, the pH adjusted to 7 with hydrochloric acid and precipitated material collected to provide 14.5 g. (63%) of hydrated 4-chloro-5-(sulfamoyl)-1,2-benzenedicarboxamide, m.p. 270°–275° C.

Anal. Calcd. for $C_8H_8ClN_3O_4S \cdot 1\ 1/3H_2O$: C, 31.85; H, 3.51; N, 13.93. Found: C, 31.73; H, 3.26; N, 14.15.

(b) A mixture of 4-chloro-5-(sulfamoyl)-1,2-benzenedicarboxamide (5.0 g., 0.018 mole) and 4-amino-1-[4-(4-methoxyphenyl)-ethyl]piperidine (4.22 g., 0.018 mole) in 50 ml. of n-pentanol was refluxed for a 24 hr. period, cooled and filtered. The filter cake, washed with methanol and then ether, provided 6-chloro-2,3-dihydro-2-[1-[2-(4-methoxyphenyl)ethyl]-4-piperidinyl]-1,3-dioxo-1H-isoindole-5-sulfonamide, 6.7 g., (78%), m.p. 195°–202° used without further purification below.

(c) Title Product

Reduction of the above part (b) 1,3-dioxoisoindole with tin according to the method of Example 1(b) afforded the title product. Purification was carried out by first treating the crude product with tetramethylenediamine in methanol, then dissolving the product in 1N sodium hydroxide and precipitation with carbon dioxide to provide 6-chloro-2,3-dihydro-2-[1-[2-(4-methoxyphenyl)ethyl]-4-piperidinyl]-3-oxo-1H-isoindole-5-sulfonamide as the dihydrate, m.p. 125°–135°.

Anal. Calcd. for $C_{22}H_{26}ClN_3O_4S \cdot 2H_2O$: C, 52.85; H, 6.05; N, 8.40; $H_2O$, 7.21. Found: C, 52.90; H, 5.52; N, 8.44; $H_2O$, 2.96.

NMR (DMSO-$d_6$): 1.75 (2H, m); 2.08 (2H, m); 2.59 (2H, m); 3.01 (2H, m); 3.35 (1H, m); 3.70 (3H, s); 4.51 (2H, s); 6.80 (2H, m); 7.11 (2H, m); 7.55 (2H, bs); 7.88 (1H, s); 8.19 (1H, s).

EXAMPLE 10

6-Chloro-2,3-dihydro-3-oxo-2-[1-[[4-(2-propenyloxy)-phenyl]methyl]-4-piperidinyl]-1H isoindole-5-sulfonamide Hydrochloride

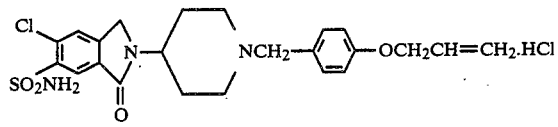

(a)
6-Chloro-2,3-dihydro-1,3-dioxo-2-[1-[[4-(2-propenyloxy)-phenyl]methy]-4-piperidinyl]-1H-isoindole-5-sulfonamide Reaction of 4-chloro-5-sulfamoylphthalimide (4.54 g., 0.0174 mole) and 4-amino-1-[4-(2-propenyloxy)benzyl]piperidine (4.29 g., 0.0174 mole) in 100 ml. of n-pentanol at reflux temperature for 24 hrs. according to the procedure of Example 1(a) afforded crude 1,3-dioxoisoindole product. Purification was carried out by treating with methanol-decolorizing charcoal followed by trituration with ether to afford 4.8 g. (57%) of the 1,3-dioxoisoindole used without further purification below.

(b) Title Product

Reduction of the above part (a) 1,3-dioxoisoindole (1.0 g., 0.002 mole) with zinc in acetic acid according to the method of Example 1(c) and conversion of the free base to the hydrochloride salt afforded 6-chloro-2,3-dihydro-3-oxo-2-[1-[[4-(2-propenyloxy)phenyl]methyl]-

4-piperidinyl]-1H-isoindole-5-sulfonamide hydrochloride as the dihydrate from methanol, m.p. 177°–180°.

Anal. Calcd. for $C_{23}H_{26}ClN_3O_4S \cdot HCl \cdot 2H_2O$: C, 50.37; H, 5.70; N, 7.66; $H_2O$, 6.57. Found: C, 50.32; H, 5.43; N, 7.80; $H_2O$, 6.42.

NMR (DMSO-$d_6$): 1.95 (2H, m); 2.30 (2H, m); 3.31 (8H, m); 4.20 (3H, m); 4.55 (4H, m); 5.31 (2H, m); 6.01 (1H, m); 7.00 (2H, m); 7.55 (2H, m); 7.75 (2H, bs); 7.93 (1H, s); 8.19 (1H, s).

EXAMPLE 11

6-Chloro-2,3-dihydro-3-oxo-2-[1-[[3-trifluoromethyl)-phenyl]methyl]-4-piperidinyl]-1H-isoindole-5-sulfonamide Hydrochloride

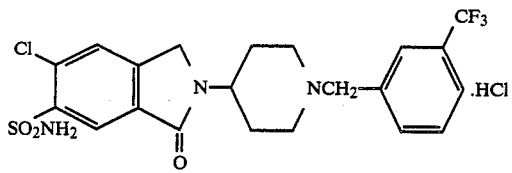

(a)
6-Chloro-2,3-dihydro-1,3-dioxo-2-[1-[[3-(trifluoromethyl)-phenyl]methyl]-4-piperidinyl]-1H-isoindole-5-sulfonamide Reaction of 4-chloro-5-sulfamoylphthalimide (10.1 g., 0.0386 mole) and 4-amino-1-(3-trifluoromethylbenzyl)piperidine (10.0 g., 0.0386 mole) in 200 ml. of n-pentanol according to the procedure of Example 1(a) afforded the crude 1,3-dioxoisoindole product purified by chromatography to yield 8.1 g. (42% yield) of 6-chloro-2,3-dihydro-1,3-dioxo-2-[1-[[3-(trifluoromethyl)-phenyl]methyl]-4-piperidinyl]-1H-isoindole-5-sulfonamide. The NMR spectral data was consistent for the compound used without further purification below.

(b)
6-Chloro-2,3-dihydro-1-hydroxy-3-oxo-2-[1-[[3-(trifluoromethyl)phenyl]methyl]-4-piperidinyl]-1H-isoindole-5-sulfonamide A mixture of the 1,3-dioxoisoindole of part (a), (8.1 g., 0.0161 mole), zinc dust (5.78 g., 0.088 mole) and 150 ml. of acetic acid was stirred for 0.5 hr. at 50°–70°, cooled. Residual material, obtained by concentration of the filtrate in vacuo, was dissolved in ethyl acetate and washed with saturated sodium bicarbonate solution and the aqueous layer re-extracted with ethyl acetate. Combined extracts were washed with saturated sodium bicarbonate, dried (MgSO$_4$) and concentrated in vacuo. Trituration of the residue with ethyl acetate provided 6-chloro-2,3-dihydro-1-hydroxy-3-oxo-2-[1-[[3-(trifluoromethyl)phenyl]methyl]-4-piperidinyl]-1H-isoindole-5-sulfonamide as a white solid, m.p. 204°–205°.

Anal. Calcd. for $C_{21}H_{21}ClF_3N_3O_4S$: C, 50.05; H, 4.20; N, 8.34. Found: C, 49.67; H, 4.10; N, 8.27.

NMR (DMSO-$d_6$): 1.80 (2H, m); 2.11 (4H, m); 2.91 (2H, m); 3.60 (2H, s); 3.85 (1H, m); 6.02 (1H, d, 8.4 Hz); 6.8 (1H, d, 8.4 Hz); 7.60 (4H, m); 7.80 (3H, m); 8.16 (1H, s).

(c) Title Product

Reduction of the part (b) 1-hydroxy compound (3.15 g., 0.0062 mole) with zinc dust (2.24 g., 0.0344 mole) in 60 ml. of acetic acid according to the method of Example 1(c) provided 2.84 g. of the free base. Conversion of the free base to the hydrochloride salt afforded 2.0 g.

(59%) of analytically pure 6-chloro-2,3-dihydro-3-oxo-2-[1-[[3-(trifluoromethyl)phenyl]methyl]-4-piperidinyl]-1H-isoindole-5-sulfonamide as the sesquihydrate, m.p. 288°–289°.

Anal. Calcd. for $C_{21}H_{21}ClF_3N_3O_3S \cdot HCl \cdot 1.5H_2O$: C, 45.74; H, 4.57; N, 7.62; $H_2O$, 4.90. Found: C, 45.34; H, 4.21; N, 7.44; $H_2O$, 4.51.

NMR (DMSO-$d_6$): 2.00 (2H, m); 2.30 (2H, m); 3.39 (4H, m); 3.52 (2H, bs); 4.42 (3H, m); 4.51 (2H, s); 7.75 (4H, m); 8.01 (3H, m); 8.19 (1H, s); 11.60 (1H, bs).

EXAMPLE 12

6-Chloro-2,3-dihydro-1-hydroxy-3-oxo-2-[1-(phenylmethyl)-4-piperidinyl]-1H-isoindole-5-sulfonamide

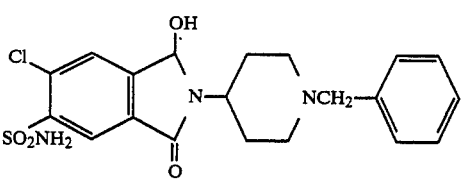

A mixture of 6-chloro-2,3-dihydro-1,3-dioxo-2-[1-(phenylmethyl)-4-piperidinyl]-1H-isoindole-5-sulfonamide (2.0 g., 4.61 mmole) and zinc dust (1.66 g., 25.4 mmole) in 60 ml. of glacial acetic acid was stirred at room temperature for 30–45 min. The mixture was filtered, the filtrate concentrated in vacuo and residual material diluted with 1:1 ethyl acetate-aqueous sodium bicarbonate. The layers were separated and the aqueous phase extracted with ethyl acetate. Combined extracts were dried (MgSO$_4$) and concentrated to about 15–20 ml. to afford a suspension of the product which was collected and dried at 80° under vacuum providing 0.98 g. (48%) of analytically pure 6-chloro-2,3-dihydro-1-hydroxy-3-oxo-2-[1-(phenylmethyl)-4-piperidinyl]-1H-isoindole-5-sulfonamide, m.p. 208°–210° (dec.).

Anal. Cacld. for $C_{20}H_{22}ClN_3O_4S$: C, 55.10; H, 5.09; N, 9.64. Found: C, 55.15; H, 5.04; N, 9.72.

NMR (DMSO-$d_6$): 1.76 (2H, m); 2.08 (4H, m); 2.90 (2H, m); 3.48 (2H, s); 3.80 (1H, m); 5.99 (1H, s); 6.78 (1H, bs); 7.28 (5H, s); 7.76 (2H, bs); 7.79 (1H, s); 8.13 (1H, s).

EXAMPLE 13

Preparation of 4-Amino-1-(phenylalkyl)-piperidine Intermediates of Formula IV (a)
1,1-Dimethylethyl[1-(phenylmethyl)-4-piperidinyl]-carbamate To a cooled mixture of N-tert.-butoxycarbonyl azide (0.448 mole) and sodium carbonate (0.91 mole) in 400 ml. of water was added 4-amino-1-benzylpiperidine (0.426 mole) over 5 minute. The resulting suspension was stirred at 5°–10° for 1 hr., allowed to warm to room temperature and then stirred an additional 24 hr. period. Dilution of the reaction mixture with 400 ml. of water, extraction with chloroform (6×300 ml.), drying and concentration of the chloroform extracts in vacuo afforded 123 g. (99%) of the tertiary butyl carbamate (a), m.p. 112°–120°.

Reaction of di-tert.-butyl pyrocarbonate (0.44 mole) with 4-amino-1-benzylpiperidine (0.4 mole) and sodium carbonate (0.5 mole) in 1:1-dioxane-water also provided the tertiary butyl carbamate (a).

(b) 1,1-Dimethylethyl 4-piperidinylcarbamate

A mixture of 1,1-dimethylethyl[1-(phenylmethyl)-4-piperidinyl]carbamate (0.355 mole), 10% palladium-on-carbon (10.0 g.) in 43 ml. of acetic acid and 90 ml. of ethanol was hydrogenated under low pressure at room temperature for a 96 hr. period. The reaction mixture was filtered and concentrated in vacuo. Residual oil was taken up in chloroform, washed with 20% aqueous sodium carbonate solution and the aqueous phase extracted with additional chloroform. The combined chloroform extracts were dried (MgSO4) and evaporated in vacuo to afford 64.2 g. (90%) of 1,1-dimethylethyl4-piperidinylcarbamate, m.p. 153°–157°.

(c) 1,1-Dimethylethyl 1-[(4-methoxyphenyl)methyl]-4-piperidinylcarbamate

A mixture of 4-(chloromethyl)anisole (0.04 mole), 1,1-dimethylethyl 4-piperidinylcarbamate (0.04 mole), potassium carbonate (0.08 mole) and potassium iodide (0.05 g.) in 250 ml. of acetonitrile was refluxed for a 16 hr. period. The hot solution was filtered and the filtrate concentrated in vacuo. Purification of the residual material was carried out chromatographically on silica gel using ethyl acetate as the eluant. Removal of the solvent in vacuo afforded 6.8 g. (53%) of 1,1-dimethylethyl 1-[(4-methoxyphenyl)-methyl]-4-piperidinylcarbamate, m.p. 95°–97°.

(d) 4-Amino-1-[(4-methoxyphenyl)methyl]piperidine

A mixture of 1,1-dimethylethyl1-[(4-methoxyphenyl)methyl]-4-piperidinylcarbamate (0.02 mole) and trifluoroacetic acid (0.01 mole) in 50 ml. of methylene chloride was refluxed for a 3 hr. period. Additional trifluoroacetic acid (0.08 mole) was added and reflux continued for an additional 30 minutes. The crude solution was evaporated in vacuo, residual material dissolved in water and the aqueous phase washed with ether and then made basic with 50% sodium hydroxide. Extraction of the basified solution with chloroform, drying of the chloroform extracts, and removal of the solvent afforded 4-amino-1-[(4-methoxyphenyl)methyl]piperidine in nearly quantitative yield.

By substituting the appropriate phenylalkyl halide for 4-(chloromethyl)anisole in step (c) above, requisite Formula IV 4-amino-1-(phenylalkyl)piperidine intermediates are obtained as illustrated by TABLE 1 below.

TABLE 1

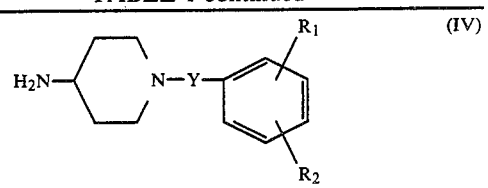

| Example No. | Y | $R_1$ | $R_2$ |
|---|---|---|---|
| 13-1 | $CH_2$ | H | H |
| 13-2 | $CH_2$ | 4-Cl | H |
| 13-3 | $CH_2$ | 4-Br | H |
| 13-4 | $CH_2$ | 4-F | H |
| 13-5 | $CH_2$ | 2-Cl | H |
| 13-6 | $CH_2$ | 4-$CH_3$ | H |
| 13-7 | $CH_2$ | 2-$CH_3$ | H |
| 13-8 | $CH_2CH_2$ | 4-$OCH_3$ | H |
| 13-9 | $CH_2$ | 4-$OCH_2CH=CH_2$ | H |
| 13-10 | $CH_2$ | 3-$CF_3$ | H |
| 13-11 | $CH_2$ | 4-$C(CH_3)_3$ | H |
| 13-12 | $CH_2$ | 4-$NO_2$ | H |
| 13-13 | $CH_2$ | 4-$CH_3S$ | H |
| 13-14 | $CH_2$ | 4-n-$C_4H_9S$ | H |
| 13-15 | $CH_2$ | 4-CN | H |
| 13-16 | $CH_2$ | 3-Cl | 4-F |
| 13-17 | —$(CH_2)_2$— | 3-Cl | 4-Cl |
| 13-18 | $CH_2$ | 3-$OCH_3$ | 4-$OCH_2CH=CH_2$ |
| 13-19 | $CH_2$ | 3-$OCH_3$ | 4-F |
| 13-20 | —$(CH_2)_2$— | H | H |
| 13-21 | $CH_2$ | 2-Cl | 4-Cl |
| 13-22 | bond | H | H |
| 13-23 | $\diagdown CH(CH_3) \diagup$ | H | H |
| 13-24 | —$(CH_2)_4$— | H | H |
| 13-25 | $CH_2$ | 3-Cl | 4-Cl |

EXAMPLE 14

Additional Compounds of Formula II

Reaction of the appropriate 4-amino-1-(phenylalkyl)-piperidine intermediate of Formula IV and 4-(halogen)-5-sulfamoylphthalimide according to the procedure of Example 1(a) provides the compounds tabulated below.

TABLE 2

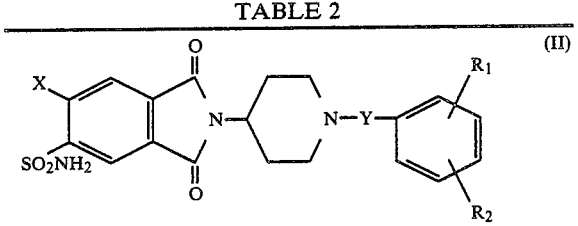

| Example No. | X | Y | $R_1$ | $R_2$ |
|---|---|---|---|---|
| 14-1 | Cl | $CH_2$ | 4-$C(CH_3)_3$ | H |

6-Chloro-2-[1-[[4-(1,1-dimethylethyl)phenyl]methyl]-4-piperidinyl]-2,3-dihydro-1,3-dioxo-1H—isoindole-5-sulfonamide Hydrochloride
Anal. Calcd. for $C_{24}H_{28}ClN_3O_4S.HCl$: C, 54.75; H, 5.55; N, 7.98. Found: C, 54.90; H, 5.80; N, 7.95.

| 14-2 | Cl | $CH_2$ | 4-$NO_2$ | H |

6-Chloro-2,3-dihydro-2-[1-[(4-nitrophenyl)methyl]-4-piperidinyl]1,3-dioxo-1H—isoindole-5-sulfonamide
Anal. Calcd. for $C_{20}H_{19}ClN_4O_6S$: C, 50.16; H, 4.00; N, 11.70. Found: C, 50.19; H, 3.98; N, 11.74

| 14-3 | Br | $CH_2$ | H | H |
| 14-4 | F | $CH_2$ | H | H |
| 14-5 | Cl | $CH_2$ | 4-$CH_3S$ | H |
| 14-6 | Cl | $CH_2$ | 4-n-$C_4H_9S$ | H |
| 14-7 | Cl | $CH_2$ | 4-CN | H |
| 14-8 | Cl | $CH_2$ | 3-Cl | 4-F |
| 14-9 | Cl | —$(CH_2)_2$— | 3-Cl | 4-Cl |
| 14-10 | Cl | $CH_2$ | 3-$OCH_3$ | 4-$OCH_2CH=CH_2$ |
| 14-11 | Cl | $CH_2$ | 3-$OCH_3$ | 4-F |
| 14-12 | Cl | —$(CH_2)_2$— | H | H |
| 14-13 | Cl | $CH_2$ | 2-Cl | 4-Cl |
| 14-14 | Cl | bond | H | H |

TABLE 2-continued

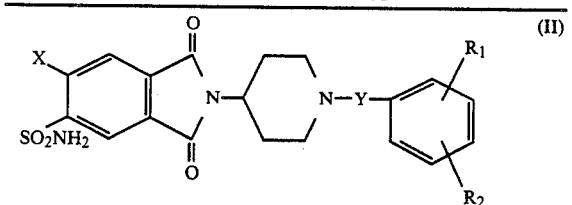

| Example No. | X | Y | R₁ | R₂ |
|---|---|---|---|---|
| 14-15 | Cl | \CH(CH₃)/ | H (m.p. 244–247°) | H |
| 14-16 | Cl | —(CH₂)₄— | H | H |
| 14-17 | Cl | CH₂ | 3-Cl | 4-Cl |

6-Chloro-2-[1-[(3,4-dichlorophenylmethyl)]-4-piperidinyl]-2,3-dihydro-1,3-dioxo-1H—isoindole-5-sulfonamide, m.p. 245–246°(dec.).
Anal. Calcd. for $C_{20}H_{18}Cl_3N_3O_4S$: C, 47.77; H, 3.61; N, 8.36.
Found: C, 47.94; H, 3.76; N, 8.64

| 14-18 | CF₃ | CH₂ | H | H |

EXAMPLE 15

Additional Compounds of Formula III

Reducing the "1,3-dioxo" compounds of Formula II described in the indicated example with zinc in glacial acetic acid according to the procedure of Example 1(c) provide the compounds tabulated below.

TABLE 3

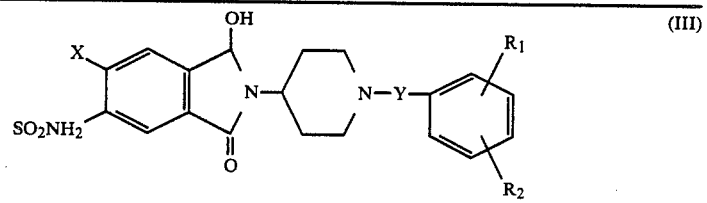

| Example No. | Starting Material Example No. | X | Y | R₁ | R₂ |
|---|---|---|---|---|---|
| 15-1 | 2 | Cl | CH₂ | 4-Cl | H |
| 15-2 | 3 | Cl | CH₂ | 4-Br | H |
| 15-3 | 4 | Cl | CH₂ | 4-F | H |
| 15-4 | 5 | Cl | CH₂ | 2-Cl | H |
| 15-5 | 6 | Cl | CH₂ | 4-CH₃ | H |
| 15-6 | 7 | Cl | CH₂ | 2-CH₃ | H |
| 15-7 | 8 | Cl | CH₂ | 4-OCH₃ | H |
| 15-8 | 9 | Cl | —(CH₂)₂— | 4-OCH₃ | H |
| 15-9 | 10 | Cl | CH₂ | 4-OCH₂CH=CH₂ | H |
| 15-10 | 14-1 | Cl | CH₂ | 4-C(CH₃)₃ | H |
| 15-11 | 14-2 | Cl | CH₂ | 4-NO₂ | H |
| 15-12 | 14-3 | Br | CH₂ | H | H |
| 15-13 | 14-4 | F | CH₂ | H | H |
| 15-14 | 14-5 | Cl | CH₂ | 4-CH₃S | H |
| 15-15 | 14-6 | Cl | CH₂ | 4-n-C₄H₉S | H |
| 15-16 | 14-7 | Cl | CH₂ | 4-CN | H |
| 15-17 | 14-8 | Cl | CH₂ | 3-Cl | 4-F |
| 15-18 | 14-9 | Cl | —(CH₂)₂— | 3-Cl | 4-Cl |
| 15-19 | 14-10 | Cl | CH₂ | 3-OCH₃ | 4-OCH₂CH=CH₂ |
| 15-20 | 14-11 | Cl | CH₂ | 3-OCH₃ | 4-F |
| 15-2 | 14-12 | Cl | —(CH₂)₂— | H | H |
| 15-22 | 14-13 | Cl | CH₂ | 2-Cl | 4-Cl |
| 15-23 | 14-14 | Cl | bond | H | H |
| 15-24 | 14-15 | Cl | \CH(CH₃)/ | H | H |
| 15-25 | 14-16 | Cl | —(CH₂)₄— | H | H |
| 15-26 | 14-17 | Cl | CH₂ | 3-Cl | 4-Cl |
| 15-27 | 14-18 | CF₃ | CH₂ | H | H |

EXAMPLE 16

Additional Compounds of Formula I

Reduction of appropriate compounds of Formula II or III set forth in TABLES 2 and 3, respectively, according to the process of the present invention provides the products tabulated below.

TABLE 4

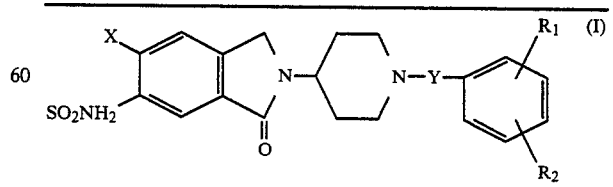

| Example No. | X | Y | R₁ | R₂ |
|---|---|---|---|---|
| 16-1 | Cl | CH₂ | 4-C(CH₃)₃ | H |
| 16-2 | Cl | CH₂ | 4-NO₂ | H |

TABLE 4-continued

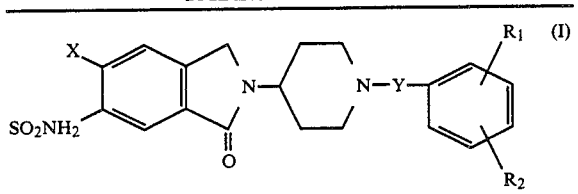

| Example No. | X | Y | R1 | R2 |
|---|---|---|---|---|
| 16-3 | Br | CH2 | H | H |
| 16-4 | F | CH2 | H | H |
| 16-5 | Cl | CH2 | 4-CH3S | H |
| 16-6 | Cl | CH2 | 4-n-C4H9S | H |
| 16-7 | Cl | CH2 | 4-CN | H |
| 16-8 | Cl | CH2 | 3-Cl | 4-F |
| 16-9 | Cl | —(CH2)2— | 3-Cl | 4-Cl |
| 16-10 | Cl | CH2 | 3-OCH3 | 4-OCH2CH=CH2 |
| 16-11 | Cl | CH2 | 3-OCH3 | 4-F |
| 16-12 | Cl | —(CH2)2— | H | H |
| 16-13 | Cl | CH2 | 2-Cl | 4-Cl |
| 16-14 | Cl | bond | H | H |
| 16-15 | Cl | >CH(CH3) | H | H |
| 16-16 | Cl | —(CH2)4— | H | H |
| 16-17 | Cl | CH2 | 3-Cl | 4-Cl |

6-Chloro-2-[1-[(3,4-dichlorophenyl)methyl]-4-piperidinyl]-2,3-dihydro-3-oxo-1H—isoindole-5-sulfonamide Hydrochloride Hydrate Anal. Calcd. for $C_{20}H_{20}Cl_3N_3O_3S \cdot HCl \cdot 1.75H_2O$: C, 43.14; H, 4.44; N, 7.55; $H_2O$, 5.66. Found: C, 43.37; H, 4.21; N, 7.80; $H_2O$, 5.56.

NMR (DMSO-$d_6$): 1.97 (2H,m); 2.30 (2H,m); 3.28 (4H,m); 3.33 (4H,bs); 4.32 (3H,m); 4.51 (2H,s); 7.75 (4H,m); 8.00 (2H,m); 8.20 (1H,s); 11.50 (1H,bs).

TABLE 4-continued

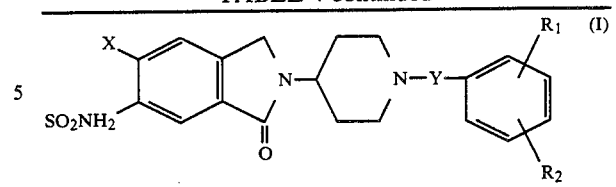

| Example No. | X | Y | R1 | R2 |
|---|---|---|---|---|
| 16-18 | CF3 | CH2 | H | H |

What is claimed is:

1. A compound of Formula II or III

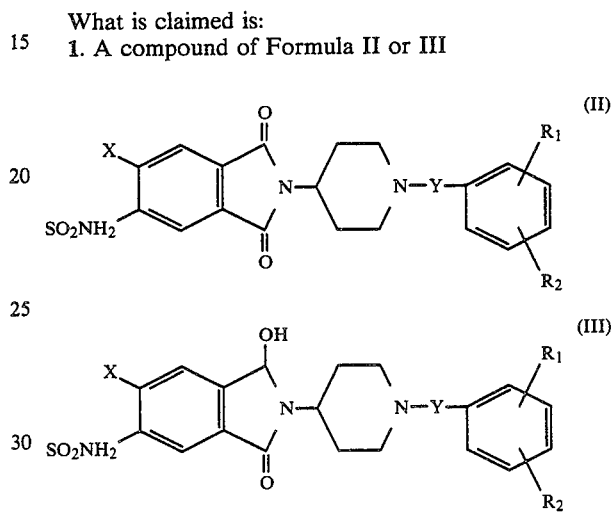

wherein
X is halogen or trifluoromethyl;
R1 and R2 are independently hydrogen, lower alkyl, lower alkoxy, lower alkenyloxy, lower alkylthio, trifluoromethyl, cyano, nitro;
Y represents a single bond or a divalent alkylene radical of 1 to 4 carbon atoms.

2. The compound of claim 1 which is 6-chloro-2,3-dihydro-1,3-dioxo-2-[1-(phenylmethyl)-4-piperidinyl]-1H-isoindole-5-sulfonamide.

3. The compound of claim 1 which is 6-chloro-2,3-dihydro-1-hydroxy-3-oxo-2-[1-(phenylmethyl)-4-piperidinyl]-1H-isoindole-5-sulfonamide.

* * * * *